United States Patent [19]
McMahon et al.

[11] Patent Number: 6,114,575
[45] Date of Patent: *Sep. 5, 2000

[54] PROCESS FOR PREPARING 2,6-NAPHTHALENEDICARBOXYLIC ACID

[75] Inventors: Rosemary F. McMahon, Wheaton, Ill.; James D. Greene, Jr., Decatur, Ala.; David A. Peterson, Westmont, Ill.

[73] Assignee: BP Amoco Corporation, Chicago, Ill.

[*] Notice: This patent issued on a continued prosecution application filed under 37 CFR 1.53(d), and is subject to the twenty year patent term provisions of 35 U.S.C. 154(a)(2).

[21] Appl. No.: 08/827,039

[22] Filed: Mar. 25, 1997

[51] Int. Cl.$^7$ .................................................. C07C 51/16
[52] U.S. Cl. ............................................ 562/414; 562/416
[58] Field of Search ...................................... 562/414, 416

[56] References Cited

U.S. PATENT DOCUMENTS

| | | |
|---|---|---|
| 3,856,855 | 12/1974 | Yamashita et al. ................. 260/524 R |
| 3,870,754 | 3/1975 | Yamashita et al. ................. 260/524 R |
| 4,709,088 | 11/1987 | Hirose .................................... 562/414 |
| 4,754,060 | 6/1988 | Hayashi ................................. 562/414 |
| 4,794,195 | 12/1988 | Hayashi ................................. 562/414 |
| 4,827,025 | 5/1989 | Shiraki ................................... 562/414 |
| 4,933,491 | 6/1990 | Albertins et al. ....................... 562/416 |
| 5,055,612 | 10/1991 | Tachibana et al. ..................... 562/416 |
| 5,183,933 | 2/1993 | Harper et al. .......................... 562/414 |
| 5,510,521 | 4/1996 | McGehee ................................ 562/414 |

FOREIGN PATENT DOCUMENTS

| | | |
|---|---|---|
| 0361840 | 9/1989 | European Pat. Off. . |
| 0600375 | 11/1993 | European Pat. Off. . |
| 56-21017 | 5/1981 | Japan ............................................ 63/38 |

Primary Examiner—Michael L. Shippen
Attorney, Agent, or Firm—Scott P. McDonald; Stephen L. Hensley

[57] ABSTRACT

A process for producing 2,6-naphthalenedicarboxylic acid by the liquid phase, exothermic oxidation of 2,6-dimethylnaphthalene comprising adding to a reaction zone oxidation reaction components comprising 2,6-dimethylnaphthalene, a source of molecular oxygen, a solvent comprising an aliphatic monocarboxylic acid, and a catalyst comprising cobalt, manganese and bromine components wherein the atom ratio of cobalt to manganese is at least about 1:1 and the total of cobalt and manganese, calculated as elemental cobalt and elemental manganese added to the reaction zone, is less than about 0.40 weight percent based on the weight of the solvent added to the reaction zone; maintaining the contents of the reaction zone at a temperature and pressure sufficient to cause the oxidation of 2,6-dimethylnaphthalene to 2,6-naphthalenedicarboxylic acid and the vaporization of at least a portion of the reaction solvent while maintaining a liquid phase reaction mixture; condensing the vaporized solvent and returning an amount of the condensed solvent to the reaction zone to maintain the amount of water in the reaction zone at no more than about 15 weight percent based on the weight of solvent in the reaction zone; and withdrawing from the reaction zone a mixture comprising 2,6-naphthalenedicarboxylic acid.

19 Claims, No Drawings

6,114,575

PROCESS FOR PREPARING 2,6-NAPHTHALENEDICARBOXYLIC ACID

FIELD OF INVENTION

This invention relates to a process for the production of 2,6-naphthalenedicarboxylic acid by the liquid phase oxidation of 2,6-dimethylnaphthalene with a molecular oxygen-containing gas. More particularly, this invention relates to a continuous process for the production of 2,6-naphthalenedicarboxylic acid in high yield by the liquid phase oxidation of 2,6-dimethylnaphthalene with a molecular oxygen-containing gas in the presence of low levels of a catalyst comprising heavy metal and bromine components.

BACKGROUND OF THE INVENTION 2,6-Naphthalenedicarboxylic acid (2,6-NDA) is a monomer useful for the preparation of high performance polymeric materials such as polyesters and polyamides. Polyethylene 2,6-naphthalate (PEN) is one such high performance polyester and it is prepared, for example, by the condensation of either 2,6-naphthalenedicarboxylic acid or dimethyl-2,6-naphthalene-dicarboxylate with ethylene glycol. Fibers and films made from PEN have improved strength and thermal properties relative to, for example, fibers and films made from polyethylene terephthalate. High strength fibers made from PEN can be used to make tire cord, and films made from PEN are advantageously used to manufacture magnetic recording tape and electronic components. Also, because of its superior resistance to gas diffusion, and particularly to the diffusion of carbon dioxide, oxygen and water vapor, films made from PEN are useful for manufacturing food containers, particularly so-called "hot fill" type food containers. Polyesters made from mixtures of terephthalic acid and 2,6-naphthalenedicarboxylic acid or dimethyl-2,6-naphthalenedicarboxylate also have been found to have unique and desirable properties such as resistance to gas diffusion, making them suitable for manufacturing, for example, beverage containers or other containers for food products.

In order to prepare high quality polyesters suitable for the aforementioned applications, it is desirable to start with purified 2,6-naphthalenedicarboxylic acid or purified dimethyl-2,6-naphthalenedicarboxylate (DM-2,6-NDC). Since dimethyl-2,6-naphthalenedicarboxylate is typically prepared by the esterification of 2,6-naphthalenedicarboxylic acid using methanol, a purer form of 2,6-naphthalenedicarboxylic acid provides for purer dimethyl-2,6-naphthalenedicarboxylate. It is therefore advantageous to have the highest purity 2,6-naphthalenedicarboxylic acid.

2,6-Naphthalenedicarboxylic acid is most conveniently prepared by the liquid phase, heavy metal catalyzed oxidation of 2,6-dimethylnaphthalene using molecular oxygen, and particularly air, as the source of oxygen for the oxidation reaction. During this oxidation, the methyl substituents on the naphthalene ring of 2,6-dimethylnaphthalene are oxidized to carboxylic acid substituents. Processes for oxidizing 2,6-dimethylnaphthalene to 2,6-naphthalenedicarboxylic acid by such a liquid phase reaction are known. For example, U.S. Pat. No. 5,183,933 to Harper et al. discloses a continuous process for oxidizing 2,6-dimethylnaphthalene to 2,6-naphthalenedicarboxylic acid using high levels of manganese and cobalt oxidation catalyst metals added to the oxidation reaction mixture.

During the liquid phase oxidation of 2,6-dimethylnaphthalene to 2,6-naphthalenedicarboxylic acid using a catalyst comprising cobalt, manganese and bromine components various side products are usually produced. For example, trimellitic acid (TMLA) is produced by the oxidation of one of the rings of the 2,6-dimethylnaphthalene molecule. 2-Formyl-6-naphthoic acid (FNA), a result of incomplete oxidation of one of the methyl groups of the 2,6-dimethylnaphthalene molecule, is also produced. Bromination of the naphthalene ring during the oxidation reaction results in the formation of bromonaphthalenedicarboxylic acid (BrNDA). Additionally, loss of one methyl (or carboxylic acid) substituent during the oxidation reaction results in the formation of 2-naphthoic acid (2-NA). These side products, as well as a collection of other unidentified side products, are undesirable because they contaminate the 2,6-naphthalenedicarboxylic acid product.

We have also determined that when high levels of catalyst metals are used to oxidize 2,6-dimethylnaphthalene to 2,6-naphthalenedicarboxylic acid, these metals tend to remain with the 2,6-naphthalenedicarboxylic acid product making it difficult to purify the 2,6-naphthalenedicarboxylic acid in subsequent purification operations. For example, when 2,6-naphthalenedicarboxylic acid is esterified to produce dimethyl-2,6-naphthalenedicarboxylate, the residual catalyst metals in the 2,6-naphthalenedicarboxylic acid product foul heat exchangers and other equipment used to manufacture dimethyl-2,6-naphthalenedicarboxylate. Also, any catalyst metal removed in such esterification processes usually results in a loss of valuable product because the metals tend to remain complexed to or suspended in 2,6-naphthalenedicarboxylic acid or dimethyl-2,6-naphthalenedicarboxylate. Therefore, it is desirable to use low levels of oxidation catalyst metals not only from the standpoint of the cost of these catalysts, but also to reduce the complexity and expense of downstream purification procedures required to prepare sufficiently pure 2,6-naphthalenedicarboxylic acid or dimethyl-2,6-naphthalenedicarboxylate.

The art needs a process for the liquid-phase oxidation of 2,6-dimethylnaphthalene suitable for large-scale commercial operations that can produce 2,6-naphthalenedicarboxylic acid in high yield and having low levels of impurities, and which produces a product which is easily purified. The present invention provides such a process.

SUMMARY OF THE INVENTION

Provided is a process for producing 2,6-naphthalenedicarboxylic acid by the liquid phase, exothermic oxidation of 2,6-dimethylnaphthalene comprising adding to a reaction zone oxidation reaction components comprising 2,6-dimethylnaphthalene, a source of molecular oxygen, a solvent comprising an aliphatic monocarboxylic acid, and a catalyst comprising cobalt, manganese and bromine components wherein the atom ratio of cobalt to manganese is at least about 1:1 and the total of cobalt and manganese, calculated as elemental cobalt and elemental manganese, is less than about 0.40 weight percent based on the weight of the solvent added to the reaction zone; maintaining the contents of the reaction zone at a temperature and pressure sufficient to cause the oxidation of 2,6-dimethylnaphthalene to 2,6-naphthalenedicarboxylic acid and the vaporization of at least a portion of the reaction solvent while maintaining a liquid phase reaction mixture; condensing the vaporized solvent and returning an amount of the condensed solvent to the reaction zone to maintain the amount of water in the reaction zone at no more than about 15 weight percent based on the weight of solvent in the reaction zone; and withdrawing from the reaction zone a mixture comprising 2,6-naphthalenedicarboxylic acid.

Also provided is a process for producing 2,6-naphthalenedicarboxylic acid by the liquid phase, exothermic oxidation of 2,6-dimethylnaphthalene in a reaction mixture comprising a low molecular weight aliphatic carboxylic acid and water, a catalyst comprising cobalt and manganese components, and a source of molecular oxygen comprising maintaining the reaction mixture in a reaction zone at a temperature and pressure sufficient to cause the oxidation of 2,6-dimethylnaphthalene to 2,6-naphthalenedicarboxylic acid; withdrawing from the reaction zone a reaction product mixture comprising 2,6-naphthalenedicarboxylic acid and reaction mother liquor; adding water and low molecular weight aliphatic carboxylic acid to the reaction product mixture withdrawn from the reaction zone to form a diluted reaction product mixture; and separating 2,6-naphthalenedicarboxylic acid from the diluted reaction product mixture.

DETAILED DESCRIPTION OF THE INVENTION

The oxidation reaction in the process of this invention is a liquid phase reaction wherein a catalyst comprising cobalt, manganese and bromine components is used to catalyze the oxidation of the methyl substituents on 2,6-dimethylnaphthalene to carboxylic acid substituents. A gas containing molecular oxygen supplies the oxygen for the oxidation reaction, and water and carbon oxides are also produced. The reaction is typically and preferably conducted in a continuous manner wherein the reaction components comprising the 2,6-dimethylnaphthalene feedstock, catalyst components, source of molecular oxygen, and solvent are continuously added to an oxidation reaction zone under predetermined reaction conditions and addition rates. In a continuous oxidation process, a reaction product mixture containing the desired 2,6-naphthalenedicarboxylic acid is typically continuously removed from the reaction zone.

During the start-up of a continuous oxidation process, the composition of the reaction mixture in the oxidation reaction zone changes as the reaction proceeds. However, after a period of time, steady state conditions are achieved and the composition of the reaction mixture in the reaction zone becomes constant, i.e., so-called "lined-out" conditions are obtained. Due to its insolubility, most of the 2,6-naphthalenedicarboxylic acid product is typically in solid form in the reaction mixture in the form of a slurry and it can be separated from the liquid part of the reaction product mixture, the so-called oxidation reaction mother liquor, by any suitable method for partitioning solids from liquids.

Prior to separating the mother liquor from 2,6-naphthalenedicarboxylic acid, the reaction mixture slurry is preferably cooled in one or more crystallizer vessels, preferably arranged in series, to crystallize 2,6-naphthalenedicarboxylic acid dissolved in the oxidation reaction mother liquor thereby maximizing recovery of the desired 2,6-naphthalenedicarboxylic acid, and also to reduce the temperature of the oxidation reaction mixture so the 2,6-naphthalenedicarboxylic acid contained therein can be separated using conventional separation equipment.

The preferred hydrocarbon feedstock for the continuous oxidation process of this invention is 2,6-dimethylnaphthalene. This feedstock can be isolated from naphthalene-containing refinery streams including so-called tar fractions, or from one or more of the various "bottoms" produced during crude oil refining processes. However, the concentration of 2,6-dimethylnaphthalene in these refinery streams is generally low and it is therefore difficult to obtain suitably large quantities of the desired 2,6-dimethylnaphthalene feedstock. An alternate and presently preferable source of 2,6-dimethylnaphthalene is from one or more of the synthetic processes known for preparing 2,6-dimethylnaphthalene. One such route starts with o-xylene and butadiene wherein the o-xylene is alkenylated in the liquid phase with butadiene in the presence of an alkali metal catalyst such as sodium and/or potassium to form 5-ortho-tolyl pentene. Such an alkenylation reaction is disclosed in U.S. Pat. No. 3,953,535 to Shima et al. The 5-ortho-tolyl pentene is subsequently cyclized to form 1,5-dimethyltetralin, which is then dehydrogenated to form 1,5-dimethylnaphthalene. The 1,5-dimethylnaphthalene is isomerized to form 2,6-dimethylnaphthalene which can be isolated as a solid product. A suitable procedure for conducting these cyclization, dehydrogenation and isomerization reactions is disclosed in U.S. Pat. No. 4,950,825 to Sikkenga et al. Another process for preparing 2,6-dimethylnaphthalene starting from m-xylene, propylene and carbon monoxide is disclosed in U.S. Pat. No. 5,023,390 to Takafumi et al. Any method or process for preparing or isolating 2,6-dimethylnaphthalene is suitable as a source of the 2,6-dimethylnaphthalene used in the process of this invention. Preferably, the 2,6-dimethylnaphthalene is at least about 98.5% and more preferably at least about 99% pure, by weight. Surprisingly, however, we have determined that the process of this invention can be used to oxidize even relatively low purity 2,6-dimethylnaphthalene, for example, 2,6-dimethylnaphthalene having purity as low as about 85% by weight. Thus, one of the advantages of the invention is the ability to use 2,6-dimethylnaphthalene of low purity.

The source of molecular oxygen employed in the liquid phase oxidation in the process of this invention can vary from pure oxygen to a gas containing about 0.1 percent by weight molecular oxygen, with the remaining gas being a ballast gas such as nitrogen that is inert in the liquid phase oxidation. Most preferably, for reasons of economy, the source of molecular oxygen is air. In order to avoid the formation of explosive mixtures, the molecular oxygen-containing gas that is introduced into the reaction zone should be added in an amount such that the exhaust gas mixture exiting the reaction zone contains from about 0.5 to 8 volume percent oxygen measured on a solvent-free basis.

The solvent used for the liquid phase oxidation reaction comprises a low molecular weight aliphatic carboxylic acid having 1 to 6 carbon atoms, a mixture of two or more of such low molecular weight carboxylic acids, or a mixture of one or more of such low molecular weight carboxylic acids with water, for example, about 1 to about 10 weight percent water. Suitable solvents include, for example, acetic acid, propionic acid, n-butyric acid and mixtures of one or more of these acids with water. Preferably, due primarily to cost and availability, the oxidation solvent added to the reaction mixture comprises acetic acid containing water, e.g., about 1 to about 10, and preferably about 5 weight percent water. Additionally, water is formed as a product of the oxidation reaction.

The oxidation reaction is an exothermic reaction and the heat generated is dissipated in part by the vaporization of the oxidation reaction solvent. Typically, a portion of the vaporized solvent or overhead is withdrawn from the reaction zone, cooled to condense the vapor, and the resulting cooled liquid is returned to the oxidation reaction mixture. The vapor is typically cooled and condensed in an overhead condenser. This vapor is a mixture of water and, when acetic acid is used as the aliphatic monocarboxylic acid solvent, acetic acid. By separating the water from the acetic acid before it is returned to the reaction zone, the water level in the reaction zone can, to a degree, be adjusted to levels lower than that which would otherwise develop in the reaction zone due to the formation of water during the oxidation reaction. We discovered that it is advantageous to operate at low levels of water in the oxidation reaction mixture, for example, water levels of no more than about 15 weight percent of the total reaction mixture in the reaction zone, more preferably less than about 10 weight percent. However, we determined that rather than separating the water from the acetic acid present in the condensed vapor, it is preferable to direct all or a portion, for example, at least about 10 weight percent, more preferably at least about 25 weight percent and most preferably at least about 40 weight percent, of such condensed stream to the oxidation reaction slurry after such slurry is withdrawn from the oxidation reaction zone and preferably to one or more of the aforementioned crystallizers used to cool the slurry mixture containing 2,6-naphthalenedicarboxylic acid after the slurry is withdrawn from the oxidation reaction zone. The addition of such condensed stream, which contains acetic acid and water, to the oxidation reaction slurry provides for a purer 2,6-naphthalenedicarboxylic acid after the 2,6-naphthalenedicarboxylic acid is separated from the diluted oxidation reaction mother liquor. In particular, it serves to reduce the levels of catalyst metals and trimellitic acid in the 2,6-naphthalenedicarboxylic acid product. The condensed stream typically comprises acetic acid and water wherein the weight ratio of acetic acid to water is in the range of about 1.5:1 to about 8:1, and more preferably in the range of about 2.3:1 to about 6.5:1. The amount of condensed stream added to the oxidation reaction slurry removed from the oxidation zone is suitably about 1 to about 200 weight percent of the oxidation reaction slurry, preferably about 20 to about 150 weight percent, and most preferably about 50 to about 100 weight percent. This addition of the condensed stream to the oxidation reaction slurry is preferably conducted in a continuous manner, i.e. the condensed stream is continuously added to the oxidation reaction slurry as the slurry is removed from the oxidation reactor. After separating the 2,6-naphthalenedicarboxylic acid from the mother liquor which preferably has been diluted with the aforementioned condensed stream, the mother liquor can be treated, typically by distillation, to recover acetic acid for recycle to the oxidation reaction mixture. A portion of the mother liquor can also be recycled to the oxidation reaction mixture.

The weight ratio of aliphatic monocarboxylic acid solvent to 2,6-dimethylnaphthalene for the liquid phase oxidation reaction, i.e., the solvent ratio, is suitably in the range of about 2:1 to about 12:1, preferably in the range of about 3:1 to about 6:1, respectively. Low ratios of monocarboxylic acid solvent to 2,6-dimethylnaphthalene, i.e. 2:1 to 6:1, are advantageous because greater amounts of 2,6-naphthalenedicarboxylic acid can be produced per reactor volume. The solvent ratio, as used herein, means the amount of solvent, by weight, in the oxidation reaction slurry withdrawn from the reaction zone divided by the amount, by weight, of 2,6-dimethylnaphthalene added to the oxidation reaction zone.

The catalyst employed in the liquid phase oxidation according to the process of this invention comprises cobalt, manganese and bromine components. Each of the cobalt and manganese components can be provided in any of its known ionic or combined forms that provides for soluble forms of cobalt and manganese in the oxidation reaction solvent. For example, one or more of cobalt and/or manganese acetate tetrahydrate, carbonate or bromide can be employed. The bromine component of the oxidation catalyst is provided by a suitable source of bromine which includes, for example, elemental bromine, i.e. $Br_2$, ionic bromide such as HBr, NaBr, KBr, $NH_4Br$, etc., or organic bromides which are known to provide bromide ions at the operating temperature of the oxidation such as, for example, benzylbromide, mono- and dibromoacetic acid, bromoacetyl bromide, tetrabromoethane, ethylene dibromide, etc.

We have determined that 2,6-dimethylnaphthalene can be oxidized to 2,6-naphthalenedicarboxylic acid having low levels of FNA, BrNDA and 2-NA using low levels of cobalt and manganese catalyst metals added to the reaction mixture provided a high ratio of cobalt to manganese is used in the oxidation reaction mixture. Thus, in the process of this invention, the atom ratio of cobalt to manganese in the oxidation reaction mixture is at least about 1:1, preferably at least about 2:1, more preferably at least about 2.5:1 and most preferably at least about 3:1. As used herein, "atom ratio" is the atomic ratio of catalyst components, for example, the ratio of milligram atoms of elemental cobalt to milligram atoms of elemental manganese, or, as discussed below, the milligram atoms of bromine measured as atomic bromine to the total of the milligram atoms of cobalt and the milligram atoms of manganese. The ratio of total cobalt and manganese catalyst metals to 2,6-dimethylnaphthalene added to the reaction mixture in gram atoms of cobalt and manganese (the total of cobalt and manganese being calculated based on elemental cobalt and elemental manganese) to moles of 2,6-dimethylnaphthalene is suitably no more than about 0.15:1, preferably no more than about 0.10:1 and most preferably no more than about 0.06:1. The total amount of cobalt and manganese, calculated as elemental cobalt and elemental manganese added to the oxidation reaction mixture, is less than about 0.40 weight percent, preferably no more than about 0.35 weight percent, and most preferably no more than about 0.30 weight percent based on the weight of solvent added to the oxidation reaction zone.

The atom ratio of the bromine component in the catalyst for the oxidation process of this invention to the total of the cobalt and manganese components, is in the range of about 0.3:1 to about 0.8:1, and preferably about 0.4:1 to about 0.7:1. If the atom ratio of bromine to the total of cobalt and manganese exceeds 0.8:1, a large amount of brominated products such as BrNDA can be formed.

The individual catalyst components can be introduced into the reaction zone where the liquid phase oxidation is occurring either separately or in one or more combinations, and they can be introduced in any convenient manner, for example, as a solution in water or a mixture of water and the monocarboxylic acid oxidation solvent, or other suitable solvent.

In the process of this invention it is advantageous to remove solvent from the oxidation reaction mixture by removing at least a portion of the condensed overhead, rather than returning all of the condensed overhead vapor or condensate to the oxidation reaction mixture. As discussed hereinabove, it is advantageous to use the condensed overhead to dilute the oxidation product slurry exiting the oxidation reaction zone. The amount of such solvent removed is preferably an amount which provides for a concentration of cobalt and manganese catalyst metal in the reaction mixture, calculated as elemental cobalt and elemental manganese, of at least about 0.10 weight percent, preferably at least about 0.20 weight percent, and more preferably at least about 0.30 weight percent based on the weight of the solvent in the reaction zone. As discussed hereinabove, removal of the overhead condensate also serves to achieve the desired low levels of water in the oxidation reaction mixture.

The reaction temperature for the liquid phase oxidation according to the process of this invention is suitably in the range of about 370° F. to about 420° F., and preferably in the range of about 380° F. to about 415° F. Reaction temperatures higher than about 420° F. or lower than about 370° F. generally cause reduced yields of the desired 2,6-naphthalenedicarboxylic acid.

The apparatus used to conduct the oxidation reaction can be a tank reactor (preferably stirred), a plug flow reactor, a compartmented reactor or a combination of two or more of these reactors. For example, the apparatus can consist of two or three stirred tank reactors arranged in series. Optionally, a plug flow reactor can suitably be used to mix and pre-heat the reactants before they enter the stirred tank reactor or reactors.

In operation, the minimum pressure at which the oxidation reaction is maintained is preferably a pressure which will maintain at least 50 weight percent and more preferably at least 70 weight percent of the solvent in the oxidation reaction zone in the liquid phase. When the solvent is a mixture of acetic acid and water, suitable reaction pressures are from about 0.1 atmosphere absolute to about 35 atmospheres absolute, and typically in the range of about 10 atmospheres absolute to about 30 atmospheres absolute.

During the oxidation reaction of this invention, 2,6-dimethylnaphthalene can be added to the oxidation reaction zone at various rates. The rate at which the 2,6-dimethylnaphthalene is added is related to the solvent ratio and the reactor residence time. As mentioned above, the solvent ratio is the amount of solvent, by weight, in the oxidation slurry withdrawn from the reaction zone divided by the amount, by weight, of 2,6-dimethylnaphthalene added to the oxidation reaction zone. The reactor residence time in minutes is the oxidation reactor drain weight in pounds divided by the reaction mixture effluent rate in pounds per minute. The solvent ratio and residence time are related to a value termed "hydrocarbon throughput" or HCTP. HCTP, as used herein, is pound moles of 2,6-dimethylnaphthalene added per cubic foot of reaction solvent in the reactor per hour, and is a measure of productivity for the oxidation reactor. HCTP is suitably in the range of about 0.02 to about 0.20, preferably about 0.04 to about 0.16, and most preferably about 0.05 to about 0.16.

The oxidation reaction mixture produced in the reaction zone during the liquid phase oxidation reaction is removed, preferably continuously, from the reaction zone typically in the form of a slurry of solid 2,6-naphthalenedicarboxylic acid in the reaction mixture mother liquor. The mother liquor typically comprises the low molecular weight monocarboxylic acid solvent, water, dissolved impurities and catalyst components. The desired 2,6-naphthalenedicarboxylic acid is separated from the mother liquor by one or more suitable methods for partitioning a solid from a liquid phase such as, for example, centrifugation, filtration, settling, etc. As discussed hereinabove, prior to this partitioning step, the oxidation reaction mixture can be cooled. The cooling can be accomplished by any convenient method, for example, a tube and shell-type heat exchanger can be used, or the reaction mixture can be cooled in a vessel equipped with cooling coils or a cooled reactor jacket. Alternatively, the reaction mixture can be added to a vessel at a pressure lower than that used for the oxidation reaction. At the reduced pressure the oxidation reaction solvent boils thereby cooling the reaction mixture. An overhead condenser can be used to cool, condense and return the overhead vapor to the vessel to further assist in the cooling. Two or more of these vessels can be used in series, each at a temperature somewhat lower than the previous vessel, to cool the reaction mixture in a stagewise manner. The oxidation reaction mixture is typically cooled to about 250° F. or below prior to partitioning the 2,6-naphthalenedicarboxylic acid from the oxidation reaction mother liquor.

After the oxidation reaction mixture exits the oxidation reaction zone, but prior to the partitioning of the 2,6-naphthalenedicarboxylic acid from the mother liquor, it is also desirable to again contact the reaction product mixture with an oxygen-containing gas in the absence of freshly added 2,6-dimethylnaphthalene. This treatment of the oxidation reaction mixture with a molecular oxygen-containing gas in the absence of freshly added 2,6-dimethylnaphthalene can be conducted at any time after the reaction mixture exits the oxidation reaction zone, and it can be conducted in any suitable manner whereby the molecular oxygen-containing gas is contacted with the reaction mixture at an elevated temperature and preferably at a temperature in the range of about 150° F. to about 450° F. Most preferably, however, the oxidation reaction mixture, as it exits the oxidation reaction zone, is directly contacted with an oxygen-containing gas in one or more suitable reactor vessels such as a tank reactor or a compartmented reactor. Advantageously, a tank reactor is used, with or without an agitator, and the molecular oxygen-containing gas is sparged into the reactor, preferably at a point at the bottom of the reactor. The temperature is suitably in the range of about 350° F. to about 450° F. Although the rate of introduction of oxygen-containing gas is not critical, there should be sufficient molecular oxygen present to oxidize the formyl group on FNA within a residence time of about 0.25 hour to about 2 hours at the temperature used. As described hereinabove, the vent gas composition must be controlled to prevent the formation of explosive mixtures. It is also possible to treat the reaction mixture with the oxygen-containing gas when the oxidation reaction mixture is being cooled, as described above. Thus, for example, while the reaction mixture is held at reduced pressure to provide for the cooling of the reaction mixture, the oxygen-containing gas is sparged through the reaction mixture. The oxygen-containing gas can contain from about 0.1 weight percent molecular oxygen to pure oxygen, with the remaining gas being an inert ballast gas such as nitrogen.

In one embodiment of the present invention water and preferably water and acetic acid (or other low molecular weight aliphatic carboxylic acid) is added to the effluent from the oxidation reaction zone in order to increase the solubility of the oxidation catalyst metals, trimellitic acid, and the products that are formed by the complexation of trimellitic acid with the cobalt and manganese oxidation catalyst metals. If the optional treatment with oxygen-containing gas is used, the addition of water or combination of water and acetic acid can occur either prior to or after the optional treatment with the oxygen-containing gas. The addition of acetic acid and water decreases the amount of metals and trimellitic acid that would otherwise be incorporated in the 2,6-naphthalenedicarboxylic acid when it is partitioned, in the manner described hereinabove, from the mother liquor.

The amount of acetic acid (or other low molecular weight aliphatic carboxylic acid) and water added to the effluent slurry from the oxidation reaction zone is an amount that provides for a purer form of 2,6-naphthalenedicarboxylic acid after it is partitioned or separated from the oxidation reaction mixture. The acetic acid and water added to the effluent slurry is suitably about 1 to about 200 weight percent of the slurry, preferably about 20 to about 150 weight percent, and most preferably about 50 to about 100 weight percent. The weight ratio of acetic acid to water added to the effluent slurry is suitably about 0.1:1 to about 10:1, more preferably about 0.2:1 to about 7:1. As described hereinabove, a preferred source of water and acetic acid for adding to the oxidation reaction effluent slurry is the mixture of acetic acid and water resulting from the condensation of the overhead vapors from the liquid phase oxidation reaction. The source of acetic acid and water can also be obtained from a scrubber or absorber used to remove acetic acid from that part of the oxidation reactor overheads which is not condensed in the overhead condenser. In this scrubber or absorber, water is used to remove or scrub the acetic acid from the gaseous, non-condensed oxidation reactor overheads. Although other sources of water, such as deionized water, and other sources of acetic acid, such as fresh acetic acid, can be added to the slurry exiting the oxidation reactor, it is advantageous to use the water and acetic acid from the absorber or from the condensed oxidation reactor overhead because such a procedure does not require the use of sources of solvent from outside the process and also because it does not add additional water to the process which must be separated from acetic acid in order to be able to reuse the valuable acetic acid. The acetic acid and water is preferably added continuously to the effluent slurry.

In another embodiment, the 2,6-naphthalenedicarboxylic acid, after its separation from the reaction mixture mother liquor, can be redispersed or reslurried in a suitable solvent such as water, a low molecular weight carboxylic acid or a mixture of water and a low molecular weight carboxylic acid at a weight ratio of about 0.1 to about 1 part of 2,6-naphthalenedicarboxylic acid per part of solvent. Preferably, at least a portion of the solvent used to redisperse or reslurry the 2,6-naphthalenedicarboxylic acid in this manner is the condensate from the overhead of the oxidation reaction mixture. After this reslurry step, the 2,6-naphthalenedicarboxylic acid can be separated from the solvent in the manner described hereinabove. The reslurry step provides for a purer 2,6-naphthalenedicarboxylic acid. The separated solvent comprising water and acetic acid can, for example, be returned, at least in part, to the oxidation reactor or it can, at least in part, be distilled to recover acetic acid for recycle to the oxidation reactor.

Mother liquor that is separated from the oxidation reaction mixture contains most of the oxidation metal catalyst components. However, the mother liquor also contains undesirable reaction side products such as trimellitic acid. Nevertheless, this mother liquor is valuable because it can be recycled, either prior to or after dilution as described hereinabove, to the oxidation reaction zone as a source of acetic acid and, more importantly, as a source of active catalyst metals. The mother liquor can be recycled to the oxidation reacting zone in an amount in the range of about 1 weight percent of the mother liquor to about 100 weight percent. Preferably, about 5 to about 50 weight percent of the mother liquor is recycled, the remaining portion typically being treated to recover the acetic acid and catalyst metals for recycle to the oxidation reaction mixture.

We have also determined that a preferred method for recycling the valuable catalyst metals to the oxidation reaction zone comprises removing the metals from the mother liquor using processes known to those of skill in the art, such as carbonate precipitation, oxalate precipitation, or by ion exchange processes such as that disclosed in U.S. Pat. No. 4,162,991. Processes from Mobile Process Technology, Inc. for removing catalyst metals from process stream are also suitable. Additionally, the mother liquor can be concentrated to recover acetic acid solvent and the residue containing oxidation catalyst metals can be incinerated. Cobalt and manganese catalyst metals from the resulting ash can be recycled to the reaction mixture.

The present invention will be more clearly understood from the following examples. It being understood, however, that these examples are presented only to illustrate embodiments of the present invention and are not intended to limit the scope thereof.

EXAMPLES

The continuous oxidations described in Examples 1 through 4 in Table I were conducted in a titanium-clad pressure reactor equipped with an agitator and overhead condensers and lines for adding the reaction components and removing the product mixture, as well as a portion of the overhead condensate stream. The reactor was maintained at an aerated slurry level of approximately 70% full. The 2,6-dimethylnaphthalene oxidation feedstock was maintained above 230° F. to keep it in the liquid state, and it was added to the reactor beneath the upper level of the aerated reactor slurry. Solvent (acetic acid containing ca. 5 weight percent water) and the catalyst components (as a solution in aqueous acetic acid) and recycled mother liquor (for Examples 1–3) obtained from the separation of 2,6-naphthalenedicarboxylic acid solids were also pumped into the reactor at controlled rates to achieve the values set forth in Table I. Compressed air was added at a rate to achieve about 2.5–3.5 volume percent oxygen in the reactor vent gas stream. The pressure in the reactor was adjusted to maintain the desired reaction temperature, typically 408° F., while allowing the heat of reaction to be removed via solvent vaporization. Vaporized solvent was condensed in the overhead condensers and returned to the oxidation reactor as reflux. The reaction mixture in the form of a slurry of 2,6-naphthalenedicarboxylic acid in mother liquor was continuously removed from the reactor and directed to a series of crystallizers where the temperature was reduced by releasing pressure. The 2,6-naphthalenedicarboxylic acid was separated from the oxidation mother liquor using a centrifuge. For Examples 1–2, water was added to the crystallizer slurry to dissolve residual catalyst metals and soluble organic impurities. This water was added either as direct addition of deionized water or as a portion of the bottoms stream from the absorber which was used to remove residual acetic acid from the reactor off-gas via scrubbing with water. For Examples 3 and 4, in addition to the water from the absorber, a portion of the reactor overhead condensate stream was also sent to the crystallizers to provide water and acetic acid to dissolve and dilute residual catalyst metals and soluble inorganic impurities from the 2,6-naphthalenedicarboxylic acid solids. Data shown in Examples 1–4 were obtained as average values over periods of time of approximately 1 week to 1 month of operation. The organic reaction products were sampled after solid/liquid separation and drying. Organic reaction products were analyzed using liquid chromatography. Catalyst metals and bromine concentrations were measured by x-ray fluorescence spectroscopy. A slip-stream from the reactor off-gas was also continuously analyzed to determine solvent-free off-gas concentrations of oxygen and carbon dioxide. The fresh cobalt and manganese catalyst components were added as an aqueous solution of their hydrated acetate salts, i.e., $Co(OAc)_2 \cdot 4H_2O$ and $Mn(OAc)_2 \cdot 4H_2O$. Bromine was added as an aqueous solution of hydrogen bromide.

In Examples 1–9, NDA is 2,6-naphthalenedicarboxylic acid, DMN is 2,6-dimethylnaphthalene, NDA isomers are other naphthalenedicarboxylic acids, LC means liquid chromatography, XRF means x-ray fluorescence spectroscopy, and EGC means esterification gas chromatography whereby the sample is treated to form the methyl ester of any carboxylic acid groups present so the sample can be analyzed by gas chromatography.

TABLE I

Effect of Co:Mn Ratio and Water Concentration

| EXAMPLE | 1 | 2 | 3 | 4 |
|---|---|---|---|---|
| Reaction Conditions | | | | |
| DMN Purity, wt. % | 95–97 | 97 | 92–94 | 97.6 |
| Co/Mn Molar Feed Ratio | 1:3 | 3:1 | 3:1 | 3:1 |
| Br/(Co + Mn) Molar Feed Ratio | 0.4 | 0.4 | 0.4 | 0.4 |
| (Co + Mn)/DMN Molar Feed Ratio | 0.114 | 0.089 | 0.055 | 0.031 |
| Wt. % Co + Mn in Solvent to Reactor[a] | 0.50 | 0.31 | 0.26 | 0.15 |
| Wt. % Co + Mn in Reactor Solvent[b] | 0.68 | 0.41 | 0.50 | 0.29 |
| Reaction Temperature, ° F. | 408 | 408 | 408 | 408 |
| Solvent Ratio[c] | 5–7 | 7–8 | 4 | 4 |
| Hydrocarbon Throughput[d] | 0.031 | 0.036 | 0.049 | 0.051 |
| Residence Time (min)[e] | 71 | 70 | 98 | 97 |
| Vol. % $O_2$ in Vent Gas[f] | 2.5 | 2.5–3.5 | 2.5 | 2.2 |
| Wt. % Water in Reactor Solvent | 10.7 | 10.5 | 8.9 | 5.6 |
| Wt. % Total Solids in Reactor Slurry | 16 | 18 | 25 | 26 |
| Wt. % Water in Crystallizer Slurry | 30 | 20 | 20 | 15–20 |
| Wt. % Total Solids in Crystallizer Slurry | 16 | 18 | 16 | 15 |
| % Mother Liquor Recycle | 20 | 20–25 | 31–35 | 0 |
| NDA Product Analyses (wt.%)[g] | | | | |
| Co + Mn | 0.28 | 0.32 | 0.24 | 0.14 |
| Br | 0.27 | 0.12 | 0.12 | 0.07 |
| TMLA | 0.22 | 0.28 | 0.45 | 0.36 |
| BrNDA | 0.44 | 0.16 | 0.09 | 0.09 |
| FNA | 0.30 | 0.16 | 0.16 | 0.15 |
| 2-NA | 0.19 | 0.17 | 0.12 | 0.09 |
| NDA Isomers[h] | 0.40 | 0.32 | 0.26 | 0.06 |

[a]Based upon aaa catalyst and solvent containing streams feeding the oxidation reactor, excluding reflux from the overhead condenser.
[b]Based upon the catalyst and solvent in the reactor effluent slurry, excluding any solvent withdrawn from the overhead condenser to reduce the water concentration in the oxidation reactor slurry.
[c]Defined as the lbs/hr of solvent in the oxidation reactor effluent slurry divided by the lbs/hr of DMN feeding the oxidation reactor.
[d]Defined as the molar feed rate of DMN in lb moles/hr divided by the volume of solvent in the oxidation reactor in $ft^3$.
[e]Defined as the oxidation reactor drain weight in lbs divided by the oxidation reactor slurry effluent rate in lbs/min.
[f]Measured on a solvent-free basis.
[g]NDA solids were recovered in a solid-bowl centrifuge, dried in a rotary dryer, and analyzed via LC and XRF.
[h]Estimated based upon 2.5 × wt. % 2,7-NDA as measured via LC analyses.

The data in Table II show the results of a series of continuous oxidation reactions performed in a manner similar to Examples 1–4.

Table I lists the results from a series of continuous oxidation runs conducted using the different ratios of cobalt to manganese catalyst metals and using different amounts of catalyst metals added to the oxidation reaction mixture. These examples demonstrate that 2,6-dimethylnaphthalene can be successfully oxidized to 2,6-naphthalenedicarboxylic acid using low levels of catalyst metals. This is demonstrated by a comparison of the results for Example 1 with the results for Examples 2–4. In Example 1, the ratio of total catalyst metals (i.e., cobalt and manganese) to 2,6-dimethylnaphthalene was 0.114 whereas in Examples 2–4, the ratio ranged from 0.089 to a low of 0.031. The analysis of the product demonstrated that, except for TMLA, the amounts of by-products were about the same or in most cases were lower for Examples 2–4 compared to Example 1. Thus, acceptable 2,6-naphthalenedicarboxylic acid was produced using a substantially reduced amount of catalyst for the amount of 2,6-dimethylnaphthalene oxidized. The results for Examples 3 and 4 demonstrate the benefits of removing from the oxidation reaction mixture a portion of the vaporized oxidation solvent produced during the exothermic oxidation reaction. In these two examples approximately one-half of the solvent added to the reaction mixture was removed by not returning to the reaction mixture all of the solvent that was vaporized and condensed. Thus, after the vaporized solvent was condensed, only a portion was returned to the oxidation reactor. This procedure was used to adjust the water concentration in the reaction mixture to the low levels reported in Table I.

The mixture of acetic acid and water removed from the oxidation reaction mixture in this manner was added to the crystallization to dissolve catalyst metals and TMLA and to dilute the mother liquor. In this manner, 2,6-naphthalenedicarboxylic acid having low levels of metals was produced.

A comparison of these results show that by using relatively high ratios of cobalt to manganese, i.e., ratios of 1:1 or greater, the amount of metal catalysts remaining with the 2,6-naphthalenedicarboxylic acid product is greatly reduced. For example, a comparison of the results for Example 5 to Example 9 in Table II show that by using a cobalt to manganese ratio of 3:1 the amount of catalyst metals on the filtered 2,6-naphthalenedicarboxylic acid was reduced by approximately 44%. TMLA concentration was also substantially reduced. Although these data show that the amount of 2-NA produced in the oxidation reaction is higher for the oxidation reaction run with a 3:1 ratio of cobalt to manganese (Example 5, Molar Reactor Yield data), the 2-NA is removed from the 2,6-naphthalenedicarboxylic acid product after it is filtered from the mother liquor.

TABLE II

Effect of Co:Mn Ratio

| EXAMPLE | 5 | 6 | 7 | 8 | 9 |
|---|---|---|---|---|---|
| Reaction Conditions | | | | | |
| DMN Purity, wt. % | 92 | 92 | 92 | 92 | 92 |
| Co/Mn Molar Feed Ratio | 3:1 | 2:1 | 1:1 | 1:2 | 1:3 |
| Br/(Co + Mn) Molar, Feed Ratio | 0.4 | 0.4. | 0.4 | 0.4 | 0.4 |
| (Co + Mn)/DMN Molar Feed Ratio | 0.084 | 0.086 | 0.083 | 0.087 | 0.090 |
| Wt. % Co + Mn in Solvent to Reactor[a] | 0.31 | 0.31 | 0.31 | 0.31 | 0.31 |
| Wt. % Co + Mn in Reactor Solvent[b] | 0.44 | 0.43 | 0.44 | 0.44 | 0.43 |
| Reaction Temperature, ° F. | 408 | 408 | 408 | 408 | 408 |
| Solvent Ratio[c] | 7.0 | 7.3 | 7.2 | 7.0 | 7.2 |
| Hydrocarbon Throughput[d] | 0.058 | 0.055 | 0.056 | 0.054 | 0.055 |
| Residence Time (min)[e] | 49 | 49 | 49 | 52 | 49 |
| Wt. % Water in Reactor Solvent | 10.0 | 9.8 | 9.5 | 9.2 | 8.7 |
| Vol.% $O_2$ in Vent Gas[f] | 2.9 | 2.9 | 2.9 | 3.1 | 3.0 |
| Vol. % CO in Vent Gas[f] | 2.5 | 2.5 | 2.1 | 1.7 | 1.4 |
| Vol. % $CO_2$ in Vent Gas[f] | 6.0 | 6.3 | 5.6 | 4.8 | 4.1 |
| Molar Reactor Yields | | | | | |
| TMLA | 4.07 | 3.92 | 3.85 | 3.79 | 4.30 |
| 2,6-NDA[g] | 91.76 | 93.82 | 94.37 | 96.14 | 95.45 |
| BrNDA | 0.11 | 0.11 | 0.13 | 0.15 | 0.20 |
| FNA | 0.31 | 0.28 | 0.32 | 0.32 | 0.42 |
| 2-NA | 1.52 | 1.33 | 1.39 | 1.18 | 1.14 |
| Filtered Cake Analyses (wt. %) | | | | | |
| Co + Mn | 0.87 | 0.94 | 1.18 | 1.41 | 1.55 |
| TMLA | 1.43 | 1.62 | 2.40 | 3.07 | 3.50 |
| BrNDA | 0.17 | 0.15 | 0.20 | 0.20 | 0.27 |
| FNA | 0.16 | 0.14 | 0.16 | 0.16 | 0.20 |
| 2-NA | 0.24 | 0.22 | 0.23 | 0.22 | 0.20 |

[a]Based upon all catalyst and solvent containing streams feeding the oxidation reactor, excluding reflux from the overhead condenser.
[b]Based upon the catalyst and solvent in the reactor effluent slurry, excluding any solvent withdrawn from the overhead condenser to reduce the water concentration in the oxidation reactor slurry.
[c]Defined as the lbs/hr of solvent in the oxidation reactor effluent slurry divided by the lbs/hr of DMN feeding the oxidation reactor.
[d]Defined as the molar feed rate of DMN in lb moles/hr divided by the volume of solvent in the oxidation reactor in $ft^3$.
[e]Defined as the oxidation reactor drain weight in lbs divided by the oxidation reactor slurry effluent rate in lbs/min.
[f]Measured on a solvent-free basis.
[g]Calculated as 100 minus the sum of yields of organic by-products measured via LC and EGC analyses and divided by DMN feed purity.

Having described the invention, that which is claimed is:
1. A process for producing 2,6-naphthalenedicarboxylic acid by the liquid phase, exothermic oxidation of 2,6-dimethylnaphthalene comprising adding to a reaction zone oxidation reaction components comprising 2,6- dimethylnaphthalene, a source of molecular oxygen, a solvent comprising an aliphatic monocarboxylic acid, and a catalyst comprising cobalt, manganese and bromine components wherein the atom ratio of cobalt to manganese is at least about 1:1 and the total of cobalt and manganese, calculated as elemental cobalt and elemental manganese added to the reaction zone, is less than about 0.40 weight percent based on the weight of the solvent added to the reaction zone; maintaining the contents of the reaction zone at a temperature and pressure sufficient to cause the oxidation of 2,6-dimethylnaphthalene to 2,6-naphthalenedicarboxylic acid and the vaporization of at least a portion of the reaction solvent while maintaining a liquid phase reaction mixture; condensing the vaporized solvent and returning an amount of the condensed solvent to the reaction zone to maintain the amount of water in the reaction zone at no more than about 15 weight percent based on the weight of solvent in the reaction zone; and withdrawing from the reaction zone a mixture comprising 2,6-naphthalenedicarboxylic acid, and wherein at least a portion of the condensed solvent is added to the mixture withdrawn from the reaction zone.

2. The process of claim 1 wherein the atom ratio of cobalt to manganese is at leas 2:1.

3. The process of claim 2 wherein the total of cobalt and manganese added to the reaction zone is no more than about 0.35 weight percent based on the weight of the solvent added to the reaction zone.

4. The process of claim 1 wherein the ratio of total cobalt and manganese catalyst metals to 2,6-dimethylnaphthalene added to the reaction zone in gram atoms of cobalt and manganese to moles of 2,6-dimethylnaphthalene is no more than about 0.15:1.

5. The process of claim 1 wherein the aliphatic monocarboxylic acid is acetic acid.

6. The process of claim 1 which is a continuous process.

7. The process of claim 1 wherein the amount of water in the reaction zone is no more than about 10 weight percent based on the weight of solvent in the reaction zone.

8. A process for producing 2,6-naphthalenedicarboxylic acid by the liquid phase, exothermic oxidation of 2,6-dimethylnaphthalene in a reaction mixture comprising a low molecular weight aliphatic carboxylic acid and water, a catalyst comprising cobalt and manganese components, and a source of molecular oxygen comprising maintaining the reaction mixture in a reaction zone at a temperature and pressure sufficient to cause the oxidation of 2,6-dimethylnaphthalene to 2,6-naphthalenedicarboxylic acid and the vaporization of at least a portion of the reaction solvent while maintaining a liquid phase reaction mixture; withdrawing from the reaction zone a reaction product mixture comprising 2,6-naphthalenedicarboxylic acid and oxidation reaction mother liquor; adding at least a portion of the vaporized reaction solvent to the product mixture to form a diluted reaction product mixture; and separating 2,6-naphthalenedicarboxylic acid from the diluted reaction product mixture.

9. The process of claim 8 wherein the atom ratio of cobalt to manganese is at least about 1:1.

10. The process of claim 9 wherein the total of cobalt and manganese added to the reaction mixture is no more than about 0.35 weight percent based on the weight of solvent added to the reaction mixture.

11. The process of claim 1 wherein the ratio of total cobalt and manganese catalyst metals to 2,6-dimethylnaphthalene added to the reaction mixture is gram atoms of cobalt and manganese to moles of 2,6-dimethylnaphthalene is no more than about 0.15:1.

12. The process of claim 8 wherein the aliphatic monocarboxylic acid is acetic acid.

13. The process of claim 8 which is a continuous process.

14. The process of claim 8 wherein the vaporized reaction solvent is condensed to a liquid prior to adding it to the product mixture.

15. The process of claim 14 wherein the amount of condensed reaction solvent added to the product mixture is about 1 to about 200 weight percent of the product mixture.

16. The process of claim 15 wherein the condensed reaction solvent comprise acetic acid and water, wherein the weight ratio of acetic acid to water is at least about 1.5:1.

17. A process for producing 2,6-naphthalenedicarboxylic acid by the liquid phase, exothermic oxidation of 2,6-dimethylnaphthalene in a reaction mixture comprising a low molecular weight aliphatic carboxylic acid in water, a catalyst comprising cobalt and manganese components where the atom ratio of cobalt to manganese is at least about 1:1, and a source of molecular oxygen comprising maintaining the reaction mixture in a reaction zone at a temperature and pressure sufficient to cause the oxidation of 2,6-dimethylnaphthalene to 2,6-naphthalenedicarboxylic acid; withdrawing from the reaction zone a reaction product mixture comprising 2,6-naphthalenedicarboxylic acid and reaction mother liquor; adding water and low molecular weight aliphatic carboxylic acid to the reaction product mixture to form a diluted reaction product mixture; and separating 2,6-naphthalenedicarboxylic acid from the diluted reaction product mixture.

18. The process of claim 17 wherein the low molecular weight aliphatic carboxylic acid is acetic acid.

19. The process of claim 17 which is a continuous process.

* * * * *